US007277178B2

(12) United States Patent
Shpantzer et al.

(10) Patent No.: US 7,277,178 B2
(45) Date of Patent: Oct. 2, 2007

(54) COHERENT PHOTOTHERMAL INTERFEROMETRIC SPECTROSCOPY SYSTEM AND METHOD FOR CHEMICAL SENSING

(75) Inventors: Isaac Shpantzer, Bethesda, MD (US); Jacob B. Khurgin, Baltimore, MD (US); Pak Shing Cho, Gaithersburg, MD (US); Yaakov Achiam, Rockville, MD (US)

(73) Assignee: Celight, Inc., Silver Spring, MD (US)

( * ) Notice: Subject to any disclaimer, the term of this patent is extended or adjusted under 35 U.S.C. 154(b) by 243 days.

(21) Appl. No.: 10/947,640

(22) Filed: Jan. 13, 2005

(65) Prior Publication Data

US 2005/0105099 A1 May 19, 2005

Related U.S. Application Data

(63) Continuation-in-part of application No. 10/669,130, filed on Sep. 22, 2003.

(60) Provisional application No. 60/582,889, filed on Jun. 25, 2004.

(51) Int. Cl.
*G01B 9/02* (2006.01)
*G01J 3/45* (2006.01)

(52) U.S. Cl. .................................................. 356/451

(58) Field of Classification Search .............. 356/128, 356/432, 451, 484, 517
See application file for complete search history.

(56) References Cited

U.S. PATENT DOCUMENTS

| 4,790,664 A | * | 12/1988 | Saito et al. ............... 356/432 |
| 4,830,502 A | * | 5/1989 | Saito et al. ............... 356/432 |
| 5,408,327 A | | 4/1995 | Geiler et al. .............. 356/432 |
| 6,038,357 A | | 3/2000 | Pan ............................ 385/24 |
| 6,709,857 B2 | | 3/2004 | Bachur, Jr. ............... 435/288.7 |
| 2004/0096143 A1 | * | 5/2004 | Shpantzer et al. ............ 385/16 |

OTHER PUBLICATIONS

E.A. McLean, "Interferometric Observation of Absorption Induced Index Change Associated with Thermal Blooming", Applied Physics Letters, vol. 13, No. 11, pp. 369-371, Dec. 1, 1968.
Frederick R. Grabiner, et al., "Laser Incudeced Time-Dependent Thermal Lensing Studies of Vibrational Relaxation: Translational Cooling in $CH_3F$", Chemical Physics Letters, vol. 17, No. 2, pp. 189-194, Nov. 15, 1972.

(Continued)

*Primary Examiner*—Gregory J. Toatley, Jr.
*Assistant Examiner*—Michael A. Lyons

(57) ABSTRACT

A photo-thermal, interferometric spectroscopy system is disclosed that provides information about a chemical at a remote location. A first light source assembly is included that emits a first beam. The first beam has one or more wavelengths that interact with the chemical and change a refractive index of the chemical. A second light source produces a second beam. The second beam interacts with the chemical resulting in a third beam with a phase change that corresponds with the change of the refractive index of the chemical. A detector system is positioned remote from the chemical to receive at least a portion of the third beam. The detector system provides information on a phase change in the third beam relative to the second beam that is indicative of at least one of, absorption spectrum and concentration of the chemical.

74 Claims, 12 Drawing Sheets

OTHER PUBLICATIONS

Leonid G. Kazovsky, "Phase-and Polarization-Diversity Coheretn Optical Techniques", Journal of Lightwave Technology, vol. 7, No. 2, pp. 279-292, Feb. 1989.

N.G. Walker, et al., "Simultaneous Phase and Amplitude Measurements on Optical Signals Using a Multiport Junction", Electronics Letters, vol. 20, No. 23, pp. 981-983, Nov. 8, 1984.

T.G. Hodkinson, et al., "Demodulation of Optical DPSK Using In-Phase and Quadrature Detection", Electronic Letters, vol. 21, No. 19, pp. 867-868, Sep. 12, 1985.

J.Saulnier, et al., "Optical Polarization-Diversity Receiver Integrated n Titanium Niobate", IEEE Photonics Technology Letters, vol. 3, No. 10, pp. 926-928, Oct. 1991.

F. Ghirardi, et al., "InP-Based 10-GHz Bandwidth Polarization Diversity Heterodyne Photoreciever with Electrooptical Adjustability", IEEE Photonics Technology Letters, vol. 6, No. 7, pp. 814-816, Jul. 1994.

D. Hoffmann, et al., "Integrated Optics Eight-Port 90° Hybrid on $LiNbO_3$", Journal of Lightwave Technology, vol. 7, No. 5, pp. 794-798, May 1989.

Harry J.R. Dutton, "Understanding Optical Communications", Prentice Hall PTR, Chapter 9, pp. 512-548, 1998.

\* cited by examiner (a)

(b)

(a)

(b)

COHERENT PHOTOTHERMAL INTERFEROMETRIC SPECTROSCOPY SYSTEM AND METHOD FOR CHEMICAL SENSING

CROSS-REFERENCE TO RELATED APPLICATIONS

This application claims the benefit of U.S. Ser. No. 60/582,889, filed Jun. 25, 2004, and is a continuation-in-part of U.S. Ser. No. 10/669,130, filed Sep. 22, 2003, both of which applications are fully incorporated herein by reference.

FIELD OF INVENTION

This invention relates generally to systems and methods for chemical detection such as explosives and others, and more particularly to photothermal interferometric spectroscopy devices, and their methods of use, based on optical signal detection.

BACKGROUND OF THE INVENTION

The principles of photothermal spectroscopy are generally described in a publication by Stephen E. Bialkowski entitled "Photothermal Spectroscopy Methods for Chemical Analysis", John Wiley & Sons, Inc., 1996, the entire content of which is incorporated by reference herein. Photothermal spectroscopy method allows carrying out extremely sensitive measurements of optical absorption in homogeneous media. It is possible, using a laser's coherent and powerful output, to obtain extremely sensitive measurements of optical absorption that exceed those of mass spectroscopy by two or three times, and produce accurate results from only a few molecules.

McLean et al. (E. A. McLean et al. American Journal Applied Physics Letters, 13, p. 369 (1968)) recognized that the optical absorption resulting in sample heating and subsequent changes in refractive index would cause a phase shift in light passing through the heated region. This phase shift can be detected by interferometric means.

Grabiner et al. (F. R. Grabiner et al. Chemical Physics Letters, 17, p. 189 (1972)) proposed to use two lasers for photothermal interferometric spectroscopy: pulsed infrared laser for the medium excitation and visible probe laser for the refractive index change measurement.

In the U.S. Pat. No. 5,408,327 a process and arrangements for photothermal spectroscopy by the single-beam method with double modulation technique is disclosed. A single-beam method is developed making use of the advantages of double modulation technique in detecting the photothermally generated difference frequency without requiring partial beams and while achieving extensive absence of intermodulation, the intensity of the laser beam is modulated before striking the object in such a way that the modulation spectrum substantially contains a carrier frequency ($f_1$) and two sideband frequencies ($f_1 +- f_2$), wherein $f_2$ is the base clock frequency of the modulation, a regulating detector and a control loop intervening in the modulation process suppress that component of the base clock frequency ($f_2$) in the same phase with the mixed frequency of the carrier frequency and sideband frequencies. After interaction with the object the optical response of the object is measured by means of a measurement detector and frequency-selective and phase-selective device as the amplitude of that component of the base clock frequency ($f_2$) which, as the photothermal mixed product, has the same phase as the mixed frequency of the carrier frequency ($f_1$) and sideband frequency ($f_1 +- f_2$). Use for nondestructive and noncontact analysis of the material parameters of areas of solid bodies close to the surface is described.

In the U.S. Pat. No. 6,709,857 a system and method for monitoring the concentration of a medium using photothermal spectroscopy is disclosed. The system and method each employs an energy emitting device, such as a laser or any other suitable type of light emitting device, which is adapted to emit a first energy signal toward a location in the container. The first energy signal has a wavelength that is substantially equal to a wavelength at which the medium absorbs the first energy signal so that absorption of the first energy signal changes a refractive index of a portion of the medium. The system and method each also employs a second energy emitting device, adapted to emit a second energy signal toward the portion of the medium while the refractive index of the portion is changed by the first energy signal, and a detector, adapted to detect a portion of the second energy signal that passes through the portion of the medium. The system and method each further employs a signal analyzer, adapted to analyze the detected portion of the second energy signal to determine an amount of a sample in the container based on a concentration of the medium in the container.

There is a need for remote methods and systems for detecting for the presence of chemicals in the field.

SUMMARY OF THE INVENTION

Accordingly, an object of the present invention is to provide improved methods and systems directed to chemical detection, such as explosives and the like.

Another object of the present invention is to provide methods and systems directed to remote detection of chemicals, such as explosives and the like.

Yet another object of the present invention is to provide photothermal interferometric spectroscopy devices, and their methods of use, for the remote detection of chemical, and the like.

Still a further object of the present invention is to provide photothermal interferometric spectroscopy devices, and their methods of use, for the remote detection of chemical, and the like, based on optical signal detection.

These and other objects of the present invention are achieved in, a photo-thermal, interferometric spectroscopy system that provides information about a chemical at a remote location. A first light source assembly is included that emits a first beam. The first beam has one or more wavelengths that interact with the chemical and change a refractive index of the chemical. A second laser produces a second beam. The second beam interacts with the chemical resulting in a third beam with a phase change that corresponds with the change of the refractive index of the chemical. A detector system is positioned remote from the chemical to receive at least a portion of the third beam. The detector system provides information on a phase change in the third beam relative to the second beam that is indicative of at least one of, absorption spectrum and concentration of the chemical.

In another embodiment of the present invention, a method is provided for determining information about a chemical at a remote location. A first beam is directed to a remote location where a chemical is present. The first beam has one or more wavelengths that interact with the chemical and changes a refractive index of the chemical. A second beam is directed to the chemical and interacts with the chemical to form a third beam. The third beam has a phase change relative to the second beam that corresponds with a change of a refractive index of the chemical. At least a portion of the third beam is received at a detection system positioned remote from the chemical. A phase shift of the third beam is measured that is induced by the first beam and is indicative of at least, one of, absorption spectrum and concentration of the chemical.

DETAILED DESCRIPTION OF THE PREFERRED EMBODIMENT

Figure 1:
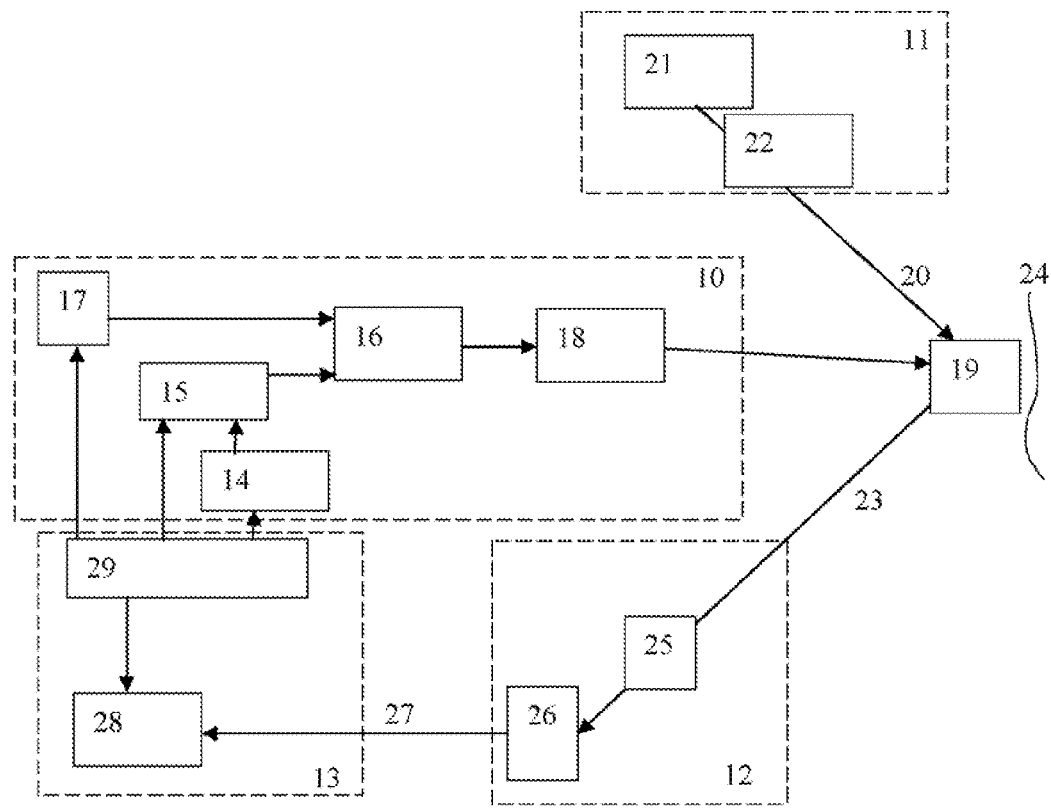
FIG. 1 is a block diagram of a photothermal interferometric spectroscopy system of the present invention that has a temporal referenced beam: (a) with reflected probe beam, (b) with transmitted probe beam.
Figure 1:
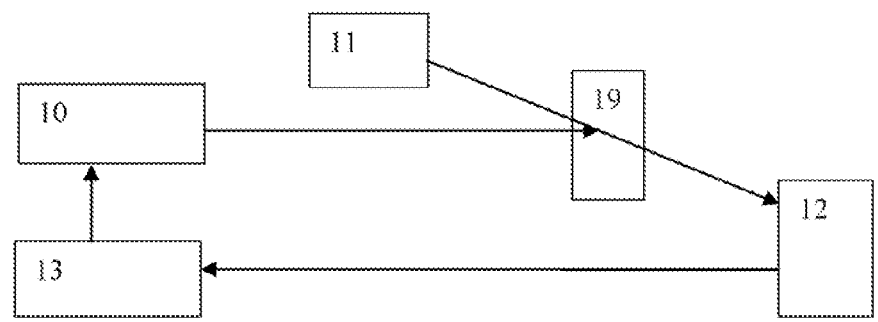

In one embodiment of the present invention, an optical device is provided, the block diagram of which is shown in FIG. 1(a), where 10 is a unit that combines strobe generation and targeting, 11 is the unit for optical probe beam generation and targeting, 12 is a signal detection and recovery block, and 13 is electronics control and processing block. The system operates as follows: the strobe laser feeds integrated wideband $Li_2NbO_3$ Optical Comb Generator 15. The comb generator 15 enables the programming and launching of very short pulses (pico-seconds) that are 'pre-shaped' in the frequency domain to match the absorption spectra of the substance under study, such as explosives or another. In the preferred embodiment the pre-shaped strobe is fed to one of the non-linear ZnSe optical mixer 16 while its other input is coupled with the Optical Parametric Oscillator (OPO) 17. The output of the mixer 16 results in strobe-spectra at the applicable absorption region of the interrogated chemical substance centered over in the wavelength range of 0.2–20 μm. The strobe beam (this beam is called "the first beam" in the present invention) is directed by targeting unit 18 to a specific location inside the examined chemical volume 19 by preferably a MEMs steering mechanism. The chemical under study is also illuminated by a probe beam (this beam is called "the second beam") or a set of beams 20 coming from the light source 21 and passing the targeting unit 22. In the preferred embodiment of the present invention, shown in FIG. 1(a), the probe set of beams 23 passed the interrogated chemical is reflected by the reflection surface 24. Collecting optics 25 collects the part of reflected light (this beam is called "the third beam") and forwards it to coherent detector 26 that includes 90-degrees optical hybrid. The electrical output signal 27 from the coherent detector is processed in DSP unit 28. Digital synthesizer and control unit 29 controls DSP unit 28, optical parametric oscillator 17, laser 14 and optical comb generator 15.

Another embodiment of the present invention is a system operating without the background reflection surface. The background surface can be eliminated if there is enough back scattered light in the interrogated chemical volume to carry out the detection.

FIG. 1(b) shows another embodiment of the present invention. This is the analogous scheme for the chemicals detection, but operating in the transmission mode. In certain situations it could be possible to install the light transmitter 11 and detector 12 on the opposite sides of the interrogated chemical volume 19. This allows the chemical detecting without background reflection surface.

The detected molecules can be brought into the excited state from which it relaxed by the following processes: (i) direct one-photon absorption; (ii) two-photons absorption and (iii) two-photons stimulated Raman process. The stimulated Raman process enables the use of less exotic light sources that simplify and optimize the overall system.

In the preferred embodiment the light of two orthogonal polarizations is used for the chemical illumination to provide complete information for data recovery.

Probing of the interrogated chemical is performed by one of two methods:

(1) Temporal referenced method,
(2) Spatial referenced method.

Temporal Referenced Method

Figure 2:
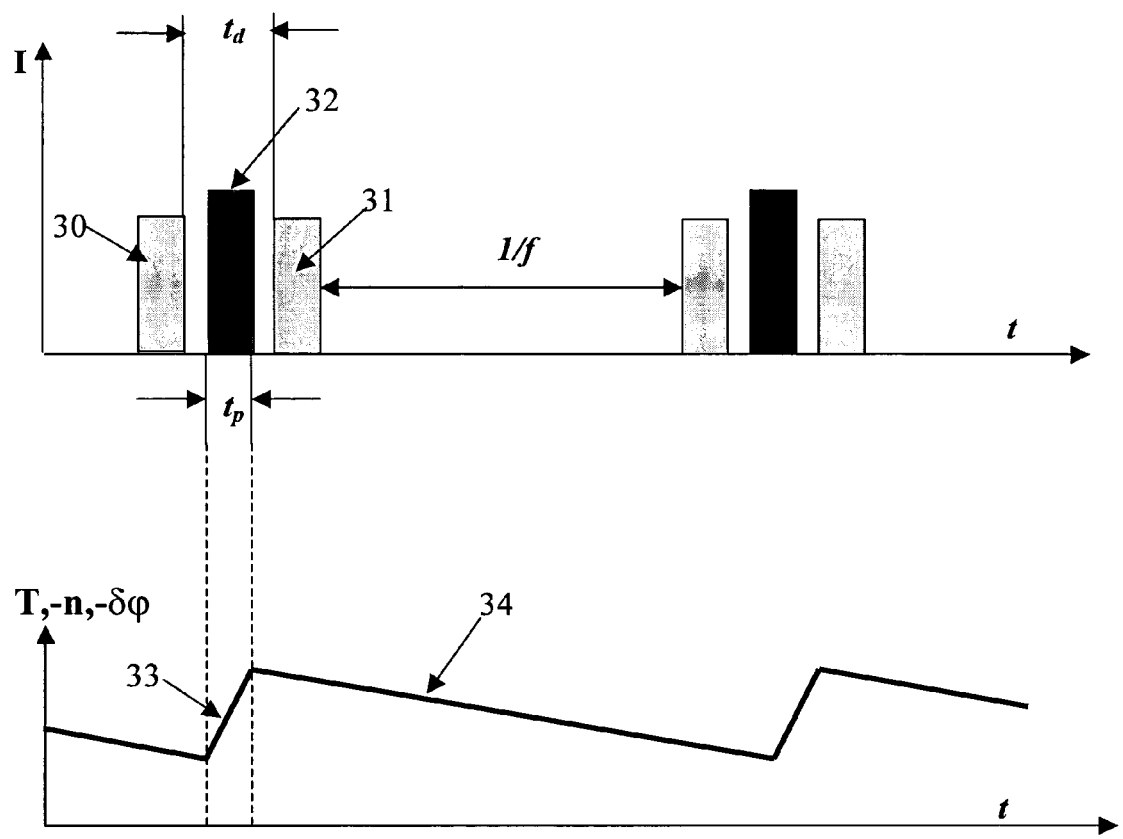
FIG. 2 illustrates a change of the refractive index of interrogated chemical and time location of the strobe and probe pulses in the case of a pair pulses probe beam in one embodiment of the present invention.

The probe pulse (FIG. 2) is split into two and recombined into a two-pulse sequence 30 and 31, separated by a time $t_d \geq t_p$ where $t_p$ is the duration of strobe pulse 32. The resulting sequence of pulses in shown in FIG. 2. The lower part of the figure shows the rapid change of the refractive index 33 in interrogated media followed by relaxation 34. The phase delay will be measured by interfering the probe signal with its time delay version using the balanced detector. Major advantage lies in the fact that if the time delay $t_d$ is short, the atmospheric noise and vibration noise are not existent. The calculations below show that the minimum detectible concentration is $10^{-10}$ $cm^{-1}$ that is better than 1 ppb.

Figure 3:
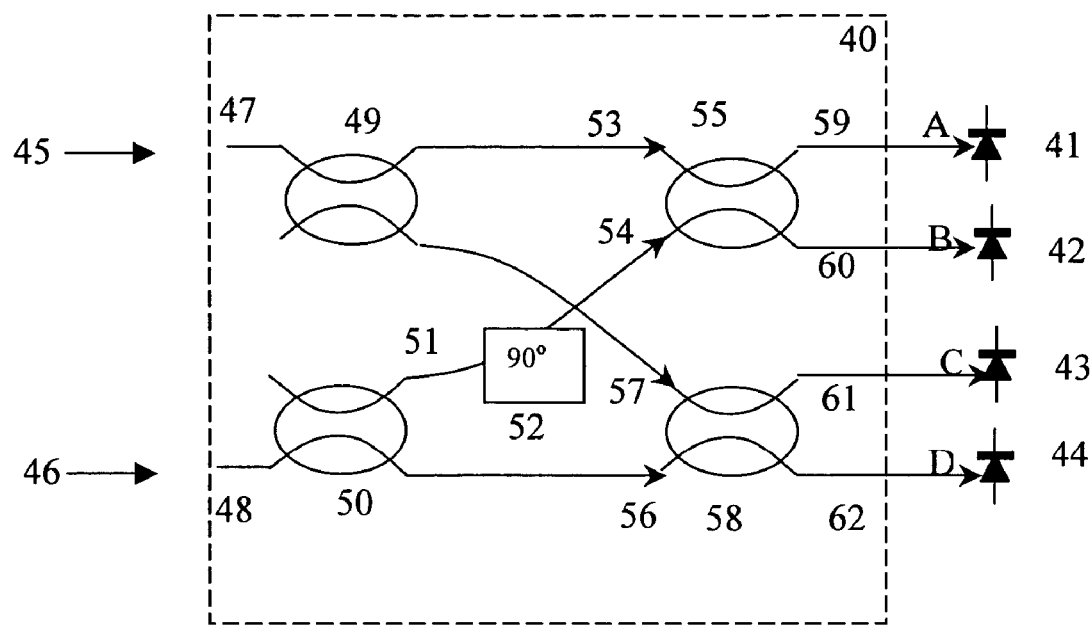
FIG. 3 is a schematic diagram of a balanced detector of the present invention with 90-degrees optical hybrid.

The interrogated chemical temperature experiences a rapid rise that leads to the rapid change of the refractive the index that causes a phase delay in the probe beam. The phase delay is measured by interfering the probe signal with its time delay version using the balanced detector. The schematic diagram of the balanced detector is shown in FIG. 3. It consists of a 90° optical hybrid 40 and four balanced photodetectors 41–44. Two incoming optical signals 45 and 46, called, respectively, the signal S and the local oscillator L, impinge two inputs 47 and 48 of the optical hybrid. Both signal beam S and local oscillator L beam are divided by the first set of 3 dB couplers 49 and 50 as shown in FIG. 3. The beam 51 passes through the phase shifter 52 and gains the additional phase shift of 90°. The beams 53 and 54 are combined together at the directional coupler 55. Respectively, the beams 56 and 57 are combined together at the directional coupler 58. The resulting four output signals A, B, C, D coming, respectively, from the outputs 59, 60, 61 and 62, all having 90° relative phase difference of the form: A=S+L, B=S−L, C=S+jL and D=S−jL.

In the preferred embodiment the balanced detector is used as described in the U.S. patent application Ser. No. 10/669,130 "Optical coherent detector and optical communications system and method" by I. Shpantzer et al. incorporated herein by reference.

Figure 4:
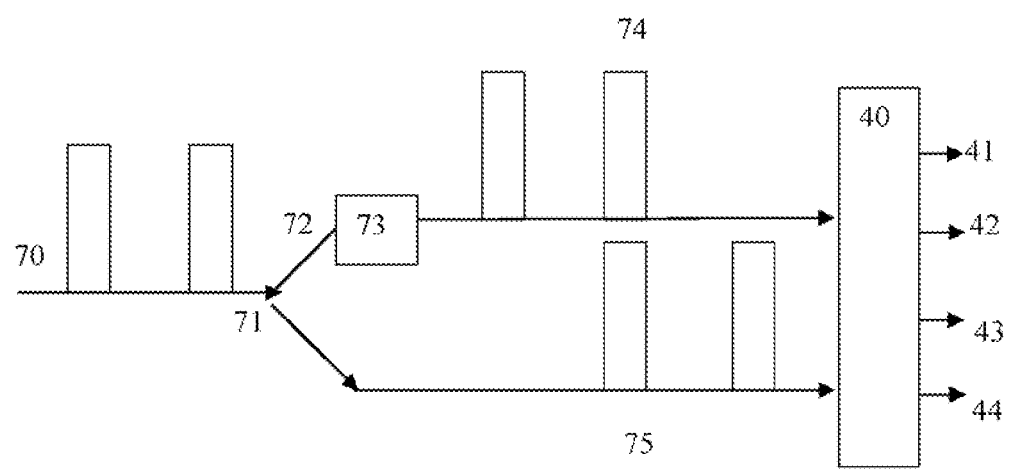
FIG. 4 illustrates interference of the pulse with the delayed pulse on the detector from FIG. 3.

FIG. 4 shows the overlapping of the time delayed signal at the detector. Incoming signal 70 is splitted at splitter 71, and the beam 72 experiences the delay at the delay line 73. The delay time is chosen to be the same as a time delay between two pulses in the pair. As the result of this delaying of one of the beams, the pulses 74 and 75 impinge the coherent detector at the same time. Since the pulse 74 corresponds to the heated chemical, and pulse 75 is the reference pulse, the information of the phase change in the laser beam due to the refractive index change can be recovered after detection.

Figure 5:
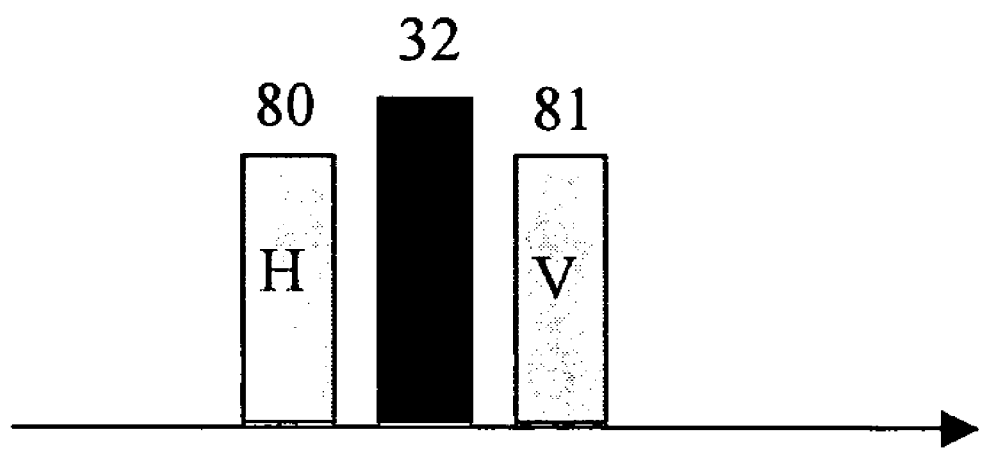
FIG. 5 illustrates a polarization multiplexed pair of pulses in one embodiment of the present invention.

Another embodiment uses polarization multiplexed configuration of probe pulses as shown in FIG. 5 in order to eliminate the delay line at the receiver. Pulse 80 and pulse 81 have orthogonal polarization states (H and V). There are various techniques to implement such polarization multiplexed dual-pulse probe laser. To help elucidate the principle an example of one such implementation is described next.

Figure 6:
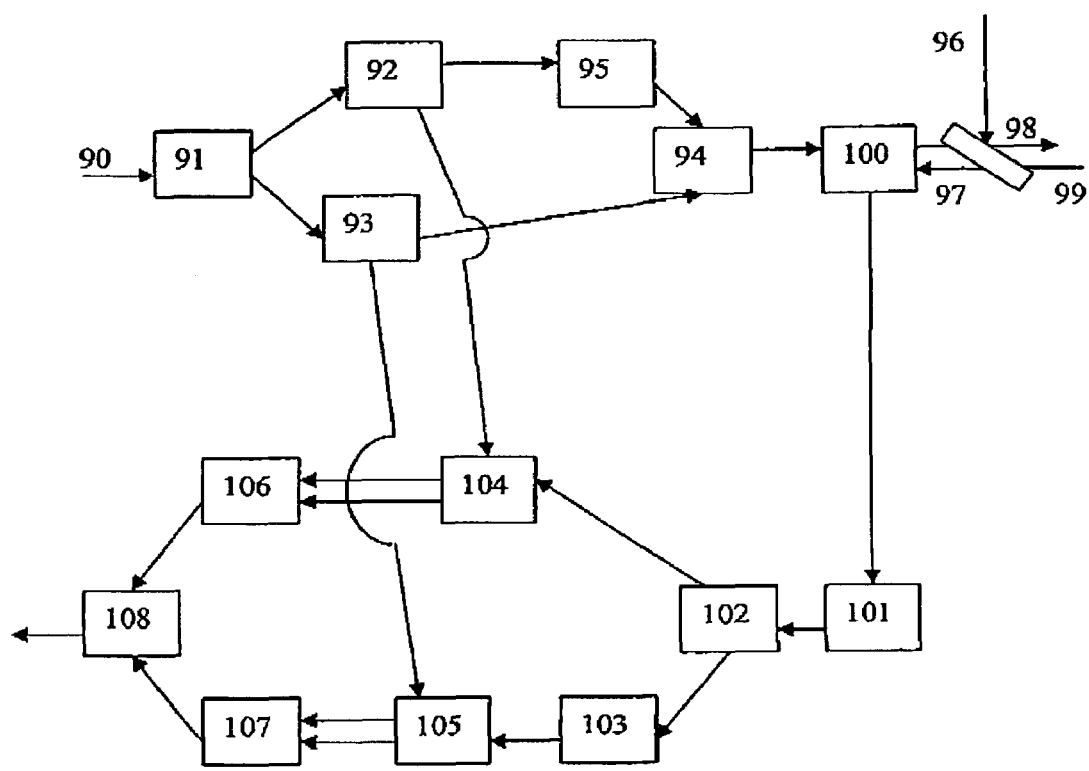
FIG. 6 illustrates polarization multiplexed signal generation and detection setup in one embodiment of the present invention.

The dual-pulse probe laser can be constructed by polarization multiplexing using a configuration shown in the FIG. 6. The input probe pulse train 90 at the far left is divided into four paths using polarization maintaining or PM fiber-optic couplers (PMCs) 91, 92, and 93. The probe pulses in two of the obtained PM optical fibers are combined orthogonally using a polarization beam combiner (PBC) 94. The two PM fibers have a relative length difference introduced by a delay line 95. It corresponds to a relative time delay, τ, which is the temporal separation of the two neighboring probe pulses. The output of the PBC is a probe pulse train with two orthogonally polarized neighboring pulses (V and H) with the H-polarized pulse delayed by τ relatively to the V-polarized pulse as shown in the FIG. 6.

Strobe pulses 96 reflected from the semitransparent mirror 97 heats up the interrogated chemical. The strobe 96 and probe 98 pulse trains are assumed to be synchronized as shown in FIG. 6.

The returned probe pulse train 99 is directed to the receiver through a circulator 100 as shown in the FIG. 6. A polarization controller 101 followed by a polarization beam splitter (PBS) 102 are used to separate the two orthogonal polarized probe pulses (V and H) into two separate optical PM fibers. The two PM fibers have a relative length difference introduced by the delay line 103. The length difference corresponds to a relative time delay, τ, similar to above but the V-polarized pulse is delayed so that the two pulses are aligned to overlap in time. The two probe pulses are combined with the two local oscillator (LO) pulses at polarization maintaining combiners 104 and 105 before impinging balanced detectors 106 and 107 as shown in the figure. The two outputs of the balanced detectors are then subtracted from each other at 108 in order to cancel out the common-path phase noise experienced by both V- and H-polarized probe pulses. The subtraction can also be performed digitally after passing the outputs of the balanced detectors to analog-to-digital converters. With digital signal processing compensation of the relative time delay of the two signals can be performed digitally thereby eliminating the fiber delay line at the receiver.

The sensitivity of the coherent detection is the following:

$$SNR_{INT} \sim \frac{\eta_2 \gamma_2}{h\nu_2} f \Delta t A^2 Q_1^2 Q_2 \left[\frac{n-1}{\lambda_2 w^2 \kappa T}\right]^2 \quad (1)$$

Here index 1 refers to the strobe and index 2 to the probe, γ is the collection efficiency, η is the detector's quantum efficiency, w is the strobe beam radius, κ is the specific heat, Q is the pulse energy, Δt is the time of measurement. The time delay $t_d$ is short that eliminates the atmospheric and vibration noises. For the same system the DIAL SNR is the following:

$$SNR_{DIAL} \sim \frac{\eta_1 \gamma_1}{4h\nu_1} f \Delta t A^2 Q_1 \quad (2)$$

Thus using the coherent detection we obtain the enhancement factor of $$E = \left[2\frac{n-1}{\lambda_2 w^2 \kappa T}\sqrt{Q_1 Q_2}\right]^2 \frac{\eta_2 \lambda_1}{\eta_1 \lambda_2} = \left[\frac{20}{w^2 \lambda_2}\sqrt{Q_1 Q_2}\right]^2 \frac{\eta_2 \lambda_1}{\eta_1 \lambda_2} \quad (3)$$

where all the energies are in Joules, the beam radius is in cm and wavelengths are in micrometers. Assuming that both strobe and probe energies are about 10 mJ in say 1 ns, the strobe wavelength is 10 μm and the probe wavelength is 1 μm. Assume furthermore distance of 100 m and the lens diameter 15 cm (w~0.4 cm). Note that 10 mJ is just about equal to the saturation energy. The enhancement factor is then of the order of E~15.

In the preferred embodiment 10 mJ pulses at required decent repetition rate are obtained using regenerative amplifiers produced by Positive Light, Santa Clara, Calif.

The estimated minimal detectable concentration is calculated below. We define the minimum change of absorption that we can detect as $A_{min} = \alpha_{min} L$, where α is absorption coefficient and L is the length of focus of the strobe laser or the size of outgasing cloud whichever is smaller $$A_{min} = \sqrt{\frac{h\nu_2}{\eta_2 \gamma_2 (f\Delta t) Q_2}} \frac{\lambda_2 w^2 \kappa T}{(n-1)Q_1} \quad (3)$$

Assuming that the frequency is 1 kHz and acquisition time is 0.1 s, and the collection efficiency is 1%. For the pulses of $A_{min}$~$10^{-7}$ or for the 10 cm path we obtain $\alpha_{min} = 10^{-8}$. Assuming that the cross-section of the absorbent is $\sigma = 10^{-18}$ cm$^2$ the minimum detectable concentration is $10^{-10}$ cm$^{-1}$. This is better than 1 ppb.

Figure 7:
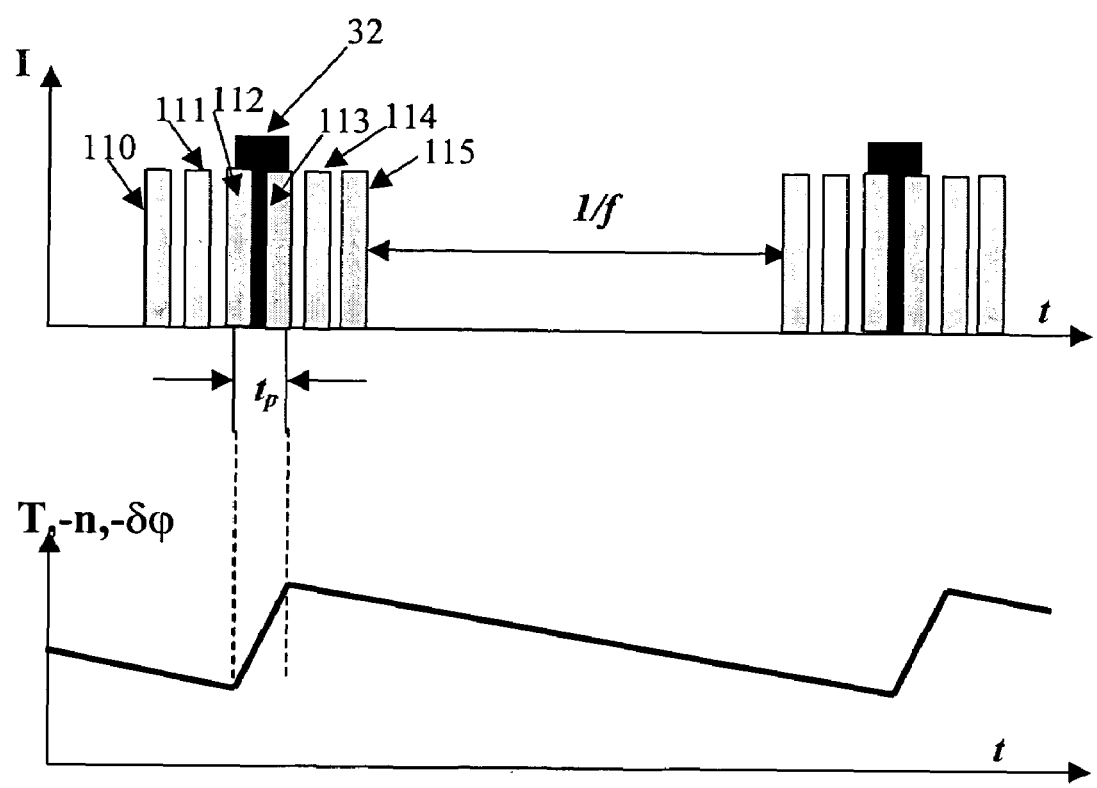
FIG. 7 illustrates the change of the refractive index of interrogated chemical and time location of the strobe and probe pulses in the case of a multiple pulses probe beam in one embodiment of the present invention.

Even better accuracy in concentration detection can be achieved if the pulse sequence 110–115, shown in FIG. 7, is used for probing.

Figure 8:
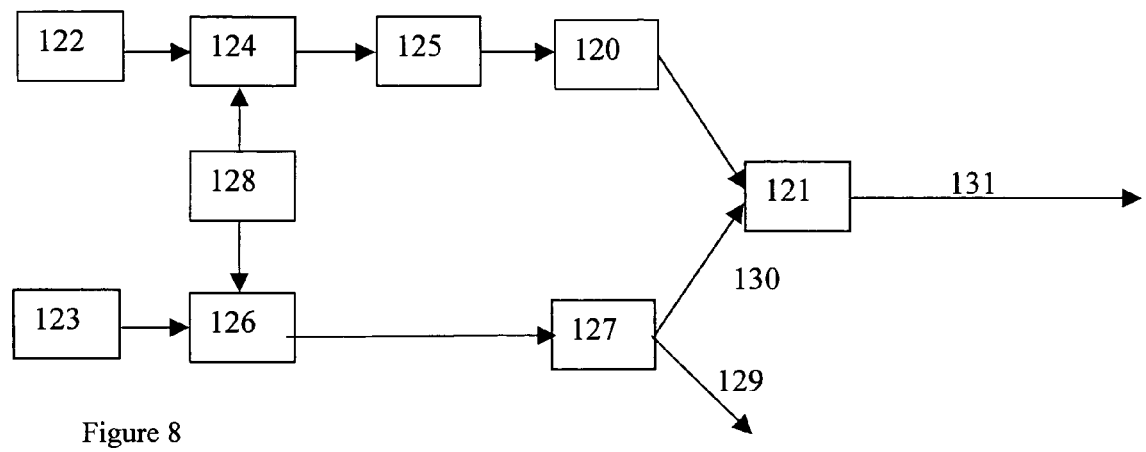
FIG. 8 is a schematic diagram of a tuneable light strobe source that is used in one embodiment of the present invention.

A schematic diagram to obtain a high power tuneable light strobe source covering whole mid-IR range is shown in FIG. 8. It is a combination of optical parametric oscillator (OPO) 120 and DFG 121 fed by two semiconductor lasers 122 and 123 operating in the 880 nm and in 980 nm range correspondingly. Periodically poled ZnSe (PPZS) serves at both OPO 120 and DFG 121 (with different pitches). The tuning can be accomplished by either temperature change or having period of PPZS graded laterally. Then moving PPZS in the lateral direction will allow the tuning.

Mode locked Yb doped fiber laser 124 consists of a gain element (Yb doped fiber) and an electro-optic modulator. The role of electro-optic modulator is to provide timing for when the mode locked pulse is generated. The pulse length of the mode-locked laser is of the order of a few picoseconds and the wavelength is 1060 nm. An Yb-doped fiber amplifier 125 boosts the power of mode locked pulses to 10 W average power.

The OPO 120 converts the 1060 nm radiation into the tunable radiation in the 1700–2800 nm ranges. It consists of the PPZS crystal placed into optical cavity.

The mode locked Er doped fiber laser 126 consists of gain element (Yb doped fiber) and electro-optic modulator. The role of electro-optic modulator is to provide timing for when the mode locked pulse is generated. The pulse length of the mode-locked laser is of the order of a few picoseconds and the wavelength is 1550 nm. An Er-doped fiber amplifier 127 that boosts the power of mode locked pulses to 10 W average power.

The clock 128 synchronizes the pulses of both Er and Yb lasers.

Following the amplifier the radiation is split into two parts: one part 129 becomes the probe radiation that measures the phase changes induced by the strobe. The other part 130, as well as the light from the Yb fiber amplifier 125 impinges upon the second PPZS crystal 121 that is not placed into optical cavity and serves as a difference frequency generator that produces pulses of tunable frequency (3.5–20 mcm) 131.

Figure 9:
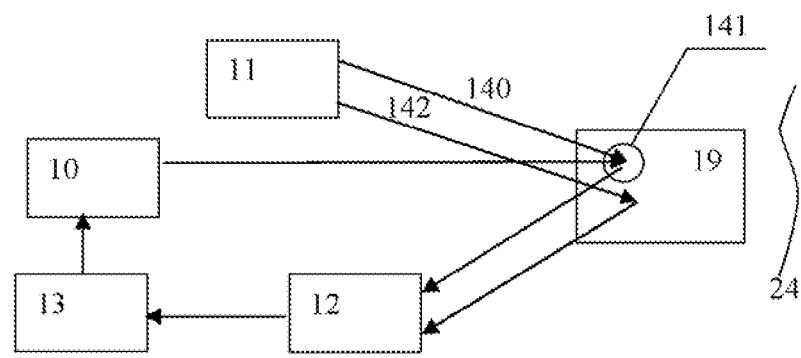
FIG. 9 is a block diagram of a photothermal interferometric spectroscopy system with a spatial referenced beam in one embodiment of the present invention.
Figure 9:
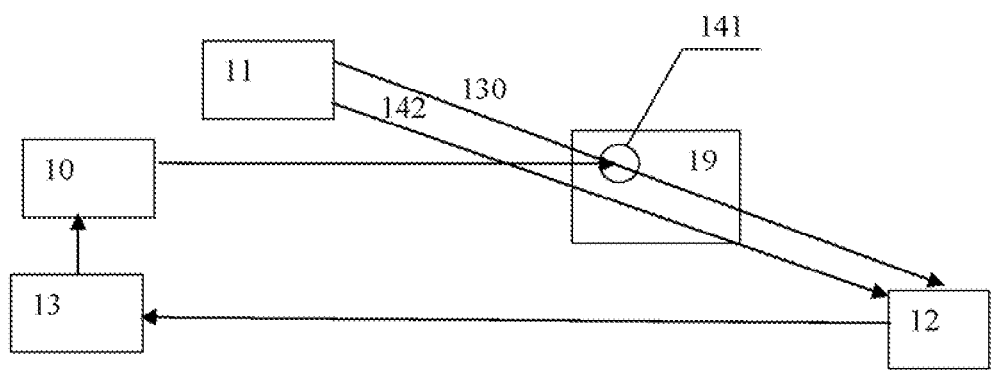

In one embodiment of the present invention, two or more probe beams are used, and they are focused on certain distance inside and near the chemical volume under study as shown in FIGS. 9(a) and (b) for reflection-type and transmission-type sensing (two beams case is shown). The probe beams generation and targeting unit 11 outputs two beams, which are slightly spatially resolved. One probe beam 140 is focused in the location of the strobe laser focus 141, and the reference probe beam 142 is focused out of the area of the strobe laser influence. After reflection from the reflective surface 24 (FIG. 9, a) two probe beams impinge the coherent detector 12. The change of phase of the first probe beam relatively to another one is recovered followed by DSP processing 13. In the preferred embodiment the coherent detector is used as described in the U.S. patent application Ser. No. 10/669,130 "Optical coherent detector and optical communications system and method" by I. Shpantzer et al. incorporated herein by reference. The information on the interrogated chemical concentration is recovered. Since the coherent detection is used the sensitivity of this system is higher (similar to time reference system) compared to the standard system described in S. E. Bialkowski, Photothermal Spectroscopy Methods for Chemical Analysis, John Wiley & Sons, Inc., 1996, incorporated herein by reference.

EXAMPLE 1

Results on Remote Gas Detection Using Photothermal Spectroscopy

In this example, preliminary test results are provided for a proof-of-concept experiment of a strobe-probe photothermal spectroscopy system of the present invention, using acetylene gas cell. In one embodiment of the present invention, systems and methods are provided to demonstrate the feasibility of using a laser beam to probe the photothermal effect in gas induced by an intense strobe laser beam, and the detection of the photothermal signal transcribed onto the probe laser beam.

Acetylene gas ($^{12}C_2H_2$) has a rich absorption lines in the range of 1510 to 1540 nm. Its absorption spectrum is well-documented and readily available. It is also commercially available in gas cell form with AR-coated end faces and optical fiber couplings.

Figure 10:
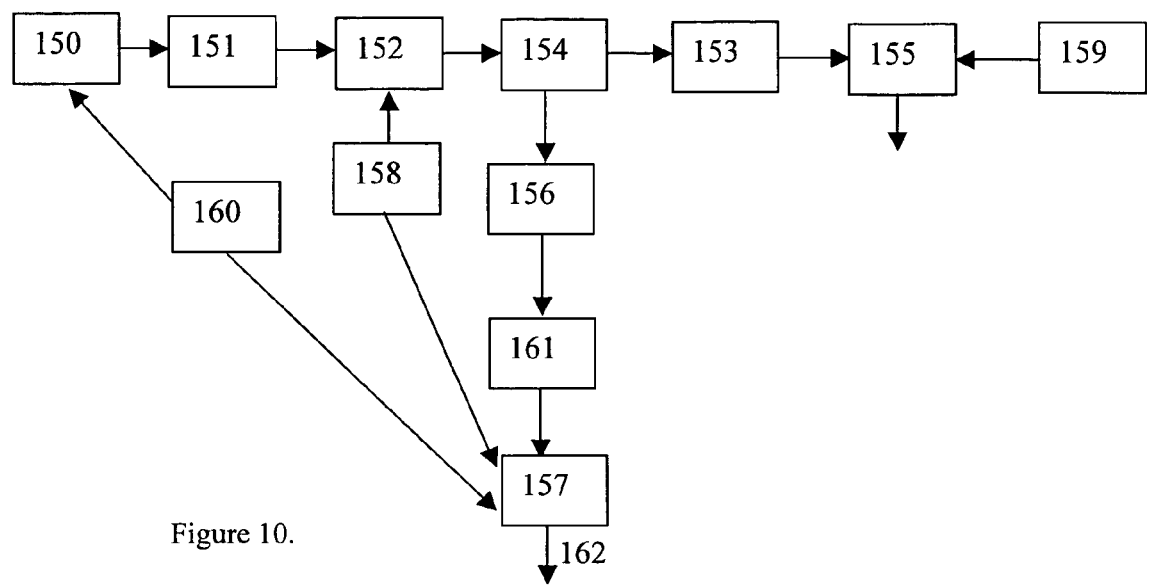
FIG. 10 illustrates an experimental setup for gas detection by a photothermal interferometric spectroscopy system in one embodiment of the present invention.
Figure 11:
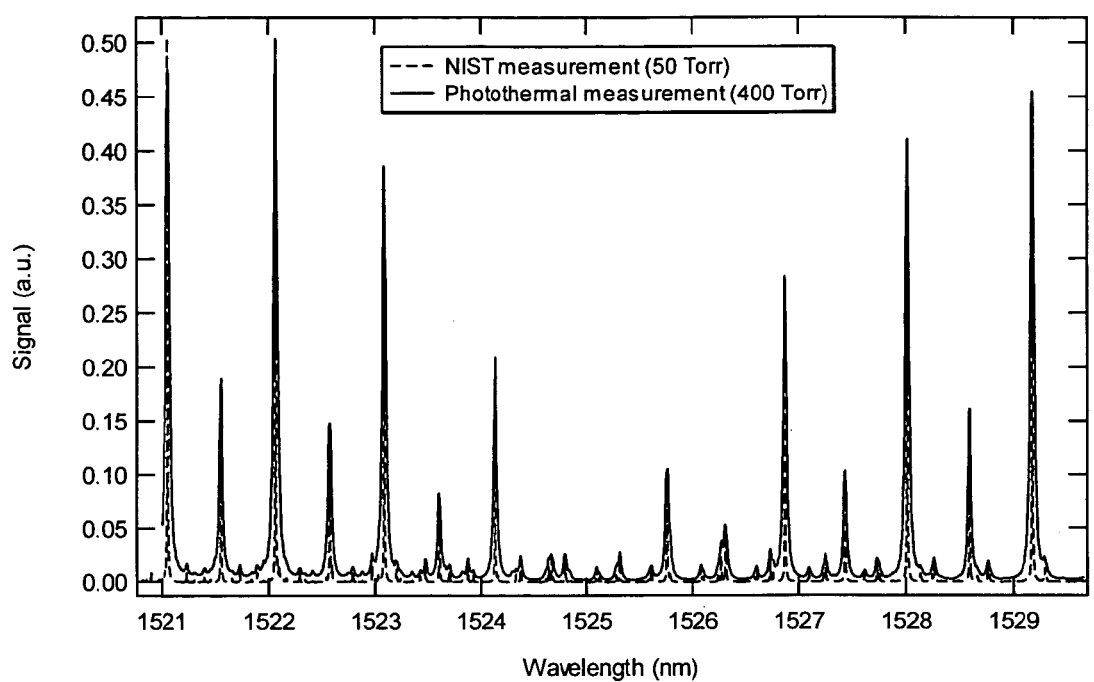
FIG. 11 illustrates experimental results on acetylene gas detection by photothermal interferometric spectroscopy from FIG. 10.

The setup for the strobe-probe photothermal measurement using direct detection is shown in FIG. 10. A tunable laser 150 with wavelength range within the acetylene absorption was used as the excitation or strobe laser. The strobe laser was amplified using an erbium-doped fiber amplifier (EDFA) 151. The amplified output was connected to a fiber U-bench 152 to direct the laser beam to free-space so that the beam can be modulated by a mechanical chopper wheel with 50% duty cycle located inside the U-bench 152. The laser beam was chopped at a frequency of $f_{strobe}$ of about 1 kHz which is lower than the lowest resonance frequency of the gas cell. The strobe is then directed to the gas cell 153 through a circulator 154. The acetylene gas pressure in the cell was 400 Torr. The strobe power to the input fiber of the gas cell was about +16 dBm (peak power). This power varies slightly with the strobe wavelength due to the gain variation of the EDFA with wavelength. The gas cell 153 has an off-resonance insertion loss of about 1 dB or 0.5 dB per interface. Therefore, the strobe power into the gas cell was about +15.5 dBm. The laser beam size within the gas cell was about 0.35 mm. A CW probe laser 159 operating at 1547.5 nm was directed (after passing the circulator 155) to the other end of the gas cell so that the strobe and the probe beams are counter-propagating. The transmitted probe beam was directed to optical bandpass filters 156 through the circulator 154. The bandpass filters reject any residual unabsorbed or reflected strobe power. A photodetector 161 was used to convert the probe laser into electrical signal, which was fed to the input of a lock-in amplifier 157 synchronized with the chopper controller 158. The probe power at the photodetector was about −5 dBm. The magnitude output 162 of the lock-in amplifier 130 ($V_{out}$) represents the photothermal signal which reflects the absorption strength of the gas. A computer 160 was used to record $V_{out}$ as the strobe laser's wavelength is tuned which was computer-controlled. FIG. 11 shows typical result of $V_{out}$ versus the strobe wavelength. The absorption spectrum of 50 Torr of acetylene gas published by NIST is also plotted for comparison.

Figure 12:
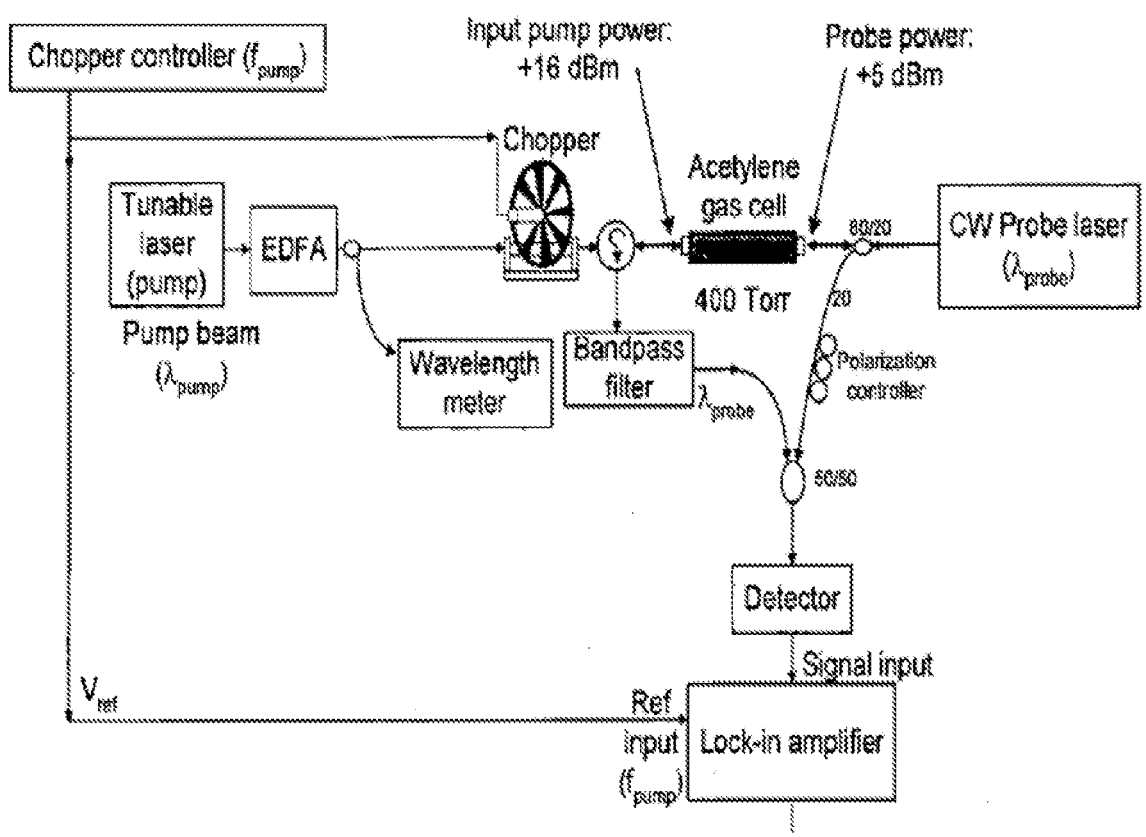
FIG. 12 illustrates an experimental setup for gas detection by photothermal spectroscopy with the probe laser divided into two paths for one embodiment of the present invention.

In this setup, direct detection converts the amplitude modulated probe signal to electrical signal. The probe laser was amplitude modulated due to thermal blooming of the probe beam as a result of the gas heating induced by the strobe laser thus reducing the refractive index. The reduction of the refractive index near the center of the beam causes a negative lens effect or divergence of the probe beam thus its intensity at the other end of the gas cell was decreased. This effect, however, is quite small and the lock-in signal at peak absorption is only about 20 mV which indicates the amplitude modulation of the probe is quite inefficiency. However, the probe is also phase modulated which can be converted to amplitude modulation using interferometric measurement. The setup shown in FIG. 12 is similar to that of FIG. 10 except that the probe laser is divided into two paths where one path was directed to the gas cell. The two paths were combined and detected. The lock-in amplifier output signal in this case increases up to 500 mV at peak absorption. The powers of the modulated and un-modulated probe laser at the detector were −17 and −11 dBm, respectively. The detector output, however, fluctuates due to random phase variation as a result of environmental perturbation of the fibers as well as laser frequency drifts. Feedback control loop can be used to compensate for such random phase variation which will be implemented in future experiments.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

The invention claimed is:

1. A photo-thermal, interferometric spectroscopy system that provides information about a chemical at a remote location, comprising:
a first light source assembly that emits a first beam, the first beam having one or more wavelengths that interact with the chemical and change a refractive index of the chemical;
a second light source that produces a second beam, the second beam interacting with the chemical resulting in a third beam with a phase change that corresponds with the change of the refractive index of the chemical; and
a detector system positioned remote from the chemical to receive at least a portion of the third beam, the detector system providing information on a phase change in the third beam relative to the second beam that is indicative of at least one of, absorption spectrum and concentration of the chemical.

2. The system of claim 1, wherein the chemical is in the form of a gas, liquid or solid.

3. The system of claim 1, wherein the chemical is incorporated in a gas, liquid or solid medium.

4. The system of claim 1, wherein the chemical is selected from, an explosive device, a fuzing and one or mere fuzing components.

5. The system of claim 1, wherein the chemical is at least one species in an explosive.

6. The system of claim 1, wherein the chemical is at an explosive site, a site of pollution and a site of a chemical weapon.

7. The system of claim 1, wherein the remote location is selected from, an explosive standoff location, outside of a blast range, inside a blast range, and at an entry point.

8. The system of claim 1, wherein the detector system is positioned from the remote location a distance that provides that the detector system does not physically touch the chemical.

9. The system of claim 1, wherein the detector system is positioned at least 1–1000 meters from the chemical.

10. The system of claim 1, wherein the detector system is configured to detect the chemical in an amount of 1 part per trillion or more.

11. The system of claim 1, wherein the first and second beams cross each other or propagating collinearly together.

12. The system of claim 1, wherein the first light source beam generates a spectrum of wavelengths in the near and far infrared ranges.

13. The system of claim 12, wherein the first light assembly, comprises: a light source that produces a light source beam; a comb generator positioned to receive the light source beam and produce a plurality of near IR wavelengths; and a non-linear mixer positioned to receive the plurality of near IR wavelengths and produce the first beam, the first beam having mid IR wavelengths that are directed to the chemical.

14. The system of claim 13, wherein the near IR wavelengths are 0.7 to 2.5 micrometer.

15. The system of claim 13, wherein the mid IR wavelengths are 2.5–20 micrometer.

16. The optical system of claim 1, wherein the first light source assembly is tuneable in a range 0.2–20 micrometer.

17. The system of claim 1, further comprising abeam directing device positioned to direct the first beam to the interrogated chemical.

18. The system of claim 17, wherein the beam directing device is selected from, a mechanical device, a minor on gimbals and a MEMS device.

19. The optical system of claim 1, wherein the second light source is a pulsed light source and the second beam is pulsed with a series of pulses.

20. The optical system of claim 19, wherein the first light source is a pulsed light source.

21. The optical system of claim 20, wherein a time between pulses of the second beam is less than equal to a time between pulses of the first beam.

22. The system of claim 19, wherein the number of pulses in a series is from 2 to N, where N is an integer up to $10^5$.

23. The system of claim 1, further comprising: a beam directing device positioned to direct the second beam to the chemical.

24. The system of claim 1 wherein the third beam is the second beam following its interaction with the chemical.

25. The system of claim 1 wherein at least one of the second and third beams pass through at least a portion of the chemical.

26. The optical system of claim 1, wherein the detector system is an interferometer.

27. The optical system of claim 1, wherein the detector system includes a coherent balanced receiver.

28. The optical system of claim 27, wherein the coherent receiver provides homodyne detection of the third beam.

29. The system of claim 27, wherein the detector system, comprises: a first coupler coupled to the first input and producing at least a first and second output; a second coupler coupled to the second input and producing at least a first and second output; a third coupler coupled to the first output of the first coupler and to the first output of the second coupler; a fourth coupler coupled to the second output of the first coupler and to the second output of the second coupler; first and second crossing waveguides with an angle selected to minimize crosstalk and losses between the first and second cross waveguides, the first crossing waveguide connecting one of the first or second outputs from the first coupler with an input of the fourth coupler, the second crossing waveguide connecting one of the first or second outputs from the second coupler with an input of the third coupler; a first phase shifter coupled to the first and second waveguides, the first and second waveguides connecting one of the outputs of the first or second coupler and one of the inputs of the third or fourth couplers, wherein the first, second, third and fourth couplers, the two crossing waveguides and the phase shifter are each formed as part of a single planar chip made of an electro-optical material.

30. The optical device of claim 27, wherein the optical device is selected from at least one of, an integrated device, a free-space optical link device, and a fiber optics device.

31. The optical device of claim 29, wherein the integrated device is a chip on one or more pieces of optical crystal.

32. The optical device of claim 27, wherein the electro-optical material is selected from at least one of, a semiconductor and a ferroelectric material.

33. The optical device of claim 32, wherein the ferroelectric material is selected from $LiNbO_3$ and $LiTaO_3$.

34. The optical system of claim 27, wherein the detector system includes a digital processor configured to measure a phase shift of the third beam that is induced by the first beam.

35. The detection system of claim 27, wherein a phase noise induced by fluctuations of a refractive index of an air path between the chemical and the detector system and vibration of a back-scattered surface is adaptively compensated using a DSP engine.

36. The system of claim 1, further comprising: a wavelengths data base that links a chemical constituent to one or more selective photo-thermal processes.

37. The system of claim 1, wherein a photo-thermal process of at least a portion of the chemical is initiated by absorption of at least a first photon from the first beam.

38. The system of claim 37, wherein a photo-thermal process of at least a portion of the chemical is initiated by populating an energy level of the chemical by a multi-photon absorption.

39. The system of claim 37, wherein a photo-thermal process of at least a portion of the chemical is initiated by populating molecular energy levels of the chemical through stimulated Raman excitation using two or more laser beams with different wavelengths.

40. The system of claim 37, wherein a photo-thermal process of at least a portion of the chemical is initiated by or more photo-thermal absorption/excitation lines of the chemical.

41. The system of claim 1, wherein detection at different wavelengths is done consequentially in time.

42. The system of claim 1, wherein the detector detects one chemical at a time.

43. The system of claim 1, wherein the detector detects a plurality of chemicals at one time.

44. The optical system of claim 1, wherein the system is configured to provide an identify of the chemical as well as isotopes of the chemical.

45. The system of claim 1, wherein the first and second beams share one or more light-sources.

46. Another embodiment includes the optical system of claim 1, wherein the second beam includes of least a first branch and a second branch, the first branch being directed into a volume that contains chemical and the second beam is directed to a position external to the chemical.

47. A method for determining information about a chemical at a remote location, comprising: directing a first beam to a remote locution where a chemical is present, the first beam having one or more wavelengths that interact with the chemical and changing a refractive index of the chemical; directing a second beam that interacts with the chemical, forming a third beam having a phase change relative to the second beam that corresponds with a change of a refractive index of the chemical; receiving at least a portion of the third beam at a detection system positioned remote from the chemical; and measuring a phase shift of the third beam that is induced by the first beam and is indicative of at least one of, absorption spectrum and concentration of the chemical.

48. The method of claim 47, wherein the chemical is in the form of a gas, liquid or solid.

49. The method of claim 47, wherein the chemical is incorporated in a gas, liquid or solid medium.

50. The method of claim 47, wherein the chemical is selected from, an explosive device, a fuzing and one or more fuzing components.

51. The method of claim 47, wherein the chemical is at least one species in an explosive.

52. The method of claim 47, wherein the chemical is at an explosive site, a site of pollution and a site of a chemical weapon.

53. The method of claim 47, wherein the remote location is selected from, an explosive standoff location, outside of a blast range, inside a blast range, and at an entry point.

54. The method of claim 47, wherein the detector system is positioned at least 1 meter from the chemical.

55. The method of claim 47, wherein the detector system is positioned at least 1–1000 meters from the chemical.

56. The method of claim 47, wherein the detector system is configured to detect the chemical in an amount of 1 part per trillion or more.

57. The method of claim 47, wherein the first and second beams cross each other or propagating collinearly together.

58. The method of claim 47, wherein the first light beam is produced from a first light source that generates a spectrum of wavelengths in near and far infrared range.

59. The method of claim 47, wherein the first light source comprises: a light source that produces a first beam; a comb generator positioned to receive the first beam to produce a beam with a plurality of near IR wavelengths; and a non-liner mixer positioned to receive the beam with the plurality of near IR wavelengths and produce the first light beam, the first beam having mid IR wavelengths that are directed to the chemical.

60. The method of claim 59, wherein the near IR wavelengths are 0.7 to 2.5 micrometer.

61. The method of claim 59, wherein the mid IR wavelengths are 2.5–20 micrometer.

62. The optical system of claim 59, wherein the first light source is tuneable in a range 0.3–20 micrometer.

63. The method of claim 47, further comprising directing the first beam with a beam directing device to the chemical.

64. The method of claim 47, wherein the second light beam is produced from a second light source, the second light source being a pulsed light source and the second beam being a pulsed beam with a series of pulses.

65. The method of claim 47, wherein the first light source is a pulsed light source.

66. The method of claim 47, wherein the second beam is a coherent pulsed beam.

67. The method of claim 66, wherein the coherent pulses beam includes a series of a plurality of a pulses in series with an interruption between each series of pulses.

68. The method of claim 67, wherein the number of pulses in a series is from 2 to N, where N is an integer up to $10^5$.

69. The method of claim 47 wherein the third beam is the second beam following its interaction with the chemical, wherein the third beam propagates in essentially the same direction as the second beam.

70. The method of claim 69 wherein the second or third beam passes through at least a portion of the chemical.

71. The method of claim 47, wherein the detector system is an interferometer.

72. The method of claim 47, wherein the detector system includes a coherent balanced receiver.

73. The method of claim 47, wherein the coherent receiver provides homodyne detection of the third beam.

74. Another embodiment of the method 47, wherein the second beam includes of least a first branch and a second branch, the first branch being directed into a volume that contains the chemical and the second beam is directed to a position external to the chemical.

* * * * *